United States Patent [19]
Greter

[11] Patent Number: 6,056,730
[45] Date of Patent: May 2, 2000

[54] DEVICE AND METHOD FOR THE DRAINAGE OF FLUIDS

[75] Inventor: Andy Greter, Steinhausen-ZG, Switzerland

[73] Assignee: Medela Holding AG, Baar, Switzerland

[21] Appl. No.: 09/019,952

[22] Filed: Feb. 6, 1998

[30] Foreign Application Priority Data

Feb. 26, 1997 [EP]  European Pat. Off. .............. 97103068

[51] Int. Cl.[7] ................................................ A61M 1/00
[52] U.S. Cl. .......................... 604/319; 604/317; 600/578
[58] Field of Search .................... 604/317, 319, 604/320, 403, 407, 408; 600/573, 577, 578; 206/514; 220/403, 404, 408, 410, 319, 287

[56]  References Cited

U.S. PATENT DOCUMENTS

| | | |
|---|---|---|
| 3,669,815 | 6/1972 | Holbrook . |
| 3,680,560 | 8/1972 | Pannier, Jr. et al. ..................... 128/276 |
| 4,063,556 | 12/1977 | Thomas et al. . |
| 4,419,903 | 12/1983 | Deaton .................................... 604/319 |
| 4,772,256 | 9/1988 | Lane et al. ................................ 604/49 |
| 4,821,896 | 4/1989 | Cheng ..................................... 215/11.3 |
| 4,870,975 | 10/1989 | Cronk et al. ............................ 128/749 |
| 5,002,534 | 3/1991 | Rosenblatt ............................... 604/319 |
| 5,269,924 | 12/1993 | Rochat .................................... 604/319 |
| 5,470,324 | 11/1995 | Cook et al. .............................. 604/319 |
| 5,713,879 | 2/1998 | Schneider ................................ 604/319 |

FOREIGN PATENT DOCUMENTS

| | | |
|---|---|---|
| 0 348 296 | 7/1990 | European Pat. Off. . |
| 2 716 806 | 9/1995 | France . |
| 3500538 | 7/1986 | Germany . |
| WO 94/14045 | 6/1994 | WIPO . |

*Primary Examiner*—Ronald Stright, Jr.
*Assistant Examiner*—David J. Cho
*Attorney, Agent, or Firm*—Baniak Nicholas Pine & Gannon

[57]  ABSTRACT

A device and method of use thereof for the drainage of fluids includes a cap, a rigid vessel and a plate-shaped top component fitted to a disposable bag. The bag with its top component is secured to a drainage aperture to form a seal with the undersurface of the plate and the rigid top component has an additional aperture fitted with a gas-permeable membrane. When a vacuum is applied, the bag opens first, followed by the creation of a vacuum inside the bag whereby the fluid is drained off via a drainage tube.

17 Claims, 2 Drawing Sheets

DEVICE AND METHOD FOR THE DRAINAGE OF FLUIDS

FIELD OF THE INVENTION

This invention is generally directed to the field of devices for the drainage of fluids, and more particularly, to devices for the drainage of body fluids during medical treatment in which the fluid is directed by vacuum via a drainage tube into a collection vessel.

BACKGROUND OF THE INVENTION

A wide range of systems and methods are currently popular for the drainage of body fluids in the field of medicine. In all those cases in which body fluids are drained and collected by the use of vacuum, this can, for example, take the form of a rigid collection vessel fitted with a cap into which, a) the drainage tube is led and, b) a connection is provided for vacuum. This connection is linked to a source of suction, such as a suction pump. The problem inherent in this type of system according to the prior art is the fact that the collection vessel has to be transported in its entirety in order to dispose of the fluids collected and, after the contents have been emptied out, this same collection vessel must be carefully cleaned. According to the current state of information, this type of system no longer fulfills the demands made on hygiene in certain cases. In order to solve this problem, it was proposed to fit a disposable bag inside the rigid vessel for the sole purpose of collecting the fluids being drained off. As described, a bag filled with fluid can be disconnected from the cap of the vessel and removed for disposal at the designated disposal point while the rigid vessel can usually be fitted with a new bag. The problem inherent in this type of system is the fact that two different vacuum tubes are required, these being one to open the bag and pull it against the inner wall of the vessel and a second connection to the inside of the bag in order to produce the required vacuum within the bag after the latter has been expanded. Care must always be taken to ensure that the vacuum in the space surrounding the bag is greater than that inside the bag as there is otherwise a danger of the bag collapsing again and preventing any further filling. Apart from these problems, a design of this type is complicated and thus expensive.

SUMMARY OF THE INVENTION

Accordingly, there is a need for a device of simple design and with the help of which the collection of fluids in flexible collection bags is made easily possible. Additionally, the basic equipment of the device and method of using the device must be suited to a system in which the fluid to be drained off can be collected by the rigid collection vessel (in cases involving non-hazardous fluids).

This need has now been solved by the present invention which includes a collection vessel having a disposable bag located in a rigid external vessel with a sealable airtight cap. According to the invention, it is possible with a single vacuum tube, first, to open up the flexible vessel located inside the airtight collection vessel and to maintain it in this position and second, to transfer the vacuum effect to the inside of the bag after the latter has opened up. In the case of opened-up bags which are always held in this desired state by means of the vacuum applied, the gas-permeable membrane ensures that no fluid can permeate the sealing membrane although air can be extracted in order to create the required vacuum according to the device and method of the invention. This simple measure, which can be achieved through the rigid top component on the bag, results in a device of exceptionally simple design that can also be used whenever disposable bags are used. In such cases, the interior of the rigid collection vessel is evacuated and the fluid drained off directly into this vessel, thus achieving universal application.

The device also includes a disposable bag that is used to collect the drained fluid and which is particularly suited to use in the device according to the invention.

During use of the device of the invention, care must be taken when using disposable bags to ensure that the walls of the bag do not simply collapse when suction becomes effective. The bag must first open up in the direction of the wall of the rigid collection vessel or must be pressed against the vessel walls. Previously, this was only possible with the use of two different vacuum connections whereby one vacuum connection served to open up the bag and the other vacuum connection served to create the vacuum inside the bag. The disadvantage of this prior art system was, first, its complicated design and, second, the fact that the effect could not always be guaranteed without making the device even more complicated.

Yet additional objects and purposes of the device and method of the present invention will be apparent to persons familiar with this field of endeavor in view of the following description, drawing figures and claims.

DETAILED DESCRIPTION OF THE INVENTION

Figure 1:
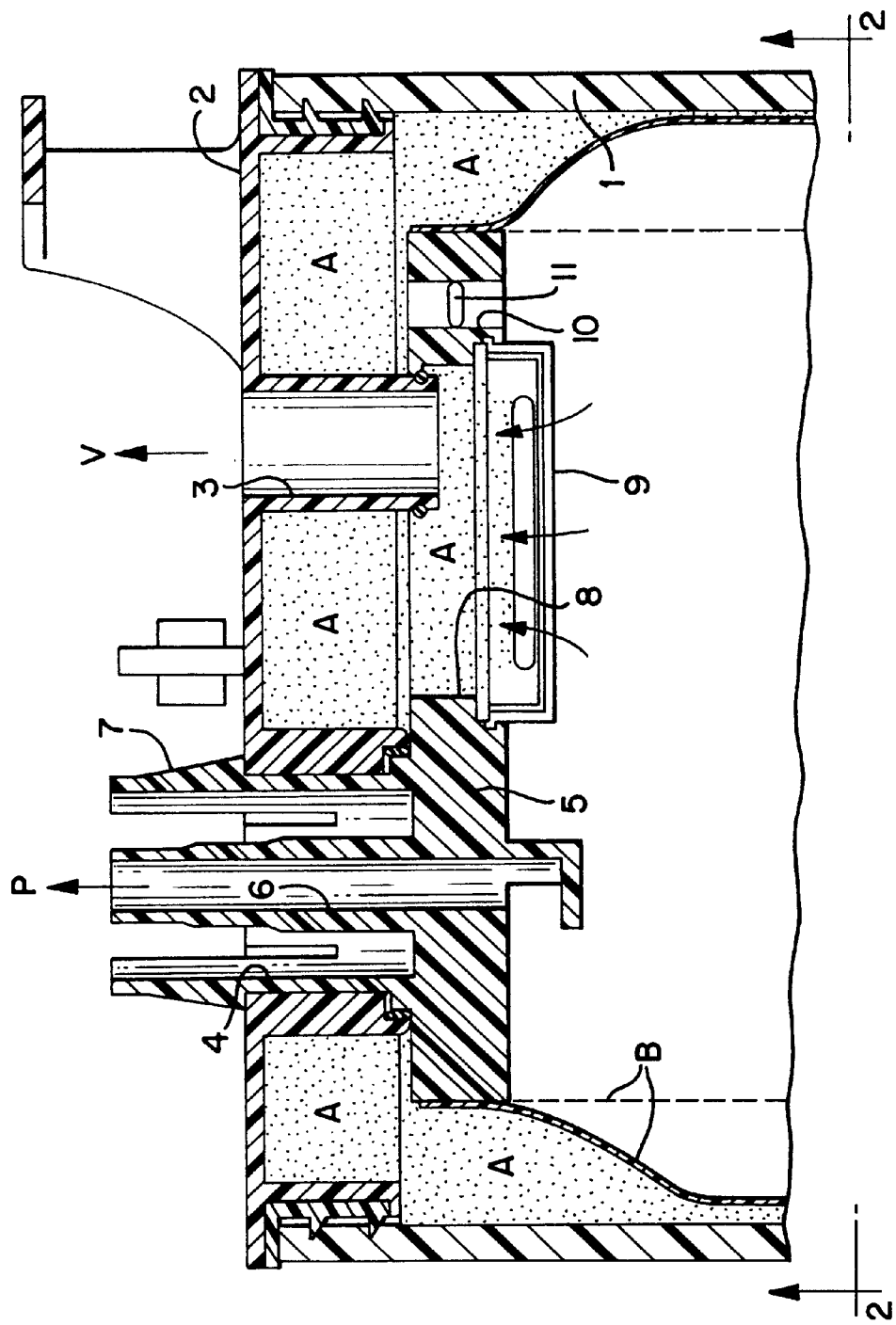
FIG. 1 is a vertical cross-sectional view of a rigid collection vessel in which a flexible disposable bag with a rigid top component is used.

The present invention will be described hereinafter with reference to the accompanying drawings. FIG. 1 shows a cap 2 is positioned on a rigid vessel 1 thereby producing an airtight closure. This is ensured by the appropriate seals between the vessel 1 and the cap 2. The cap 2 has a connection aperture 3 for the attachment of a connection tube to a suction source indicated by arrow V such as a suction pump (not shown for the sake of clarity) to which the connection tube can also be fitted or otherwise attached to form an airtight seal. The vessel cap 2 also has an attachment aperture 4 for the fitting of a drain tube (not shown) leading to the patient.

Figure 2:
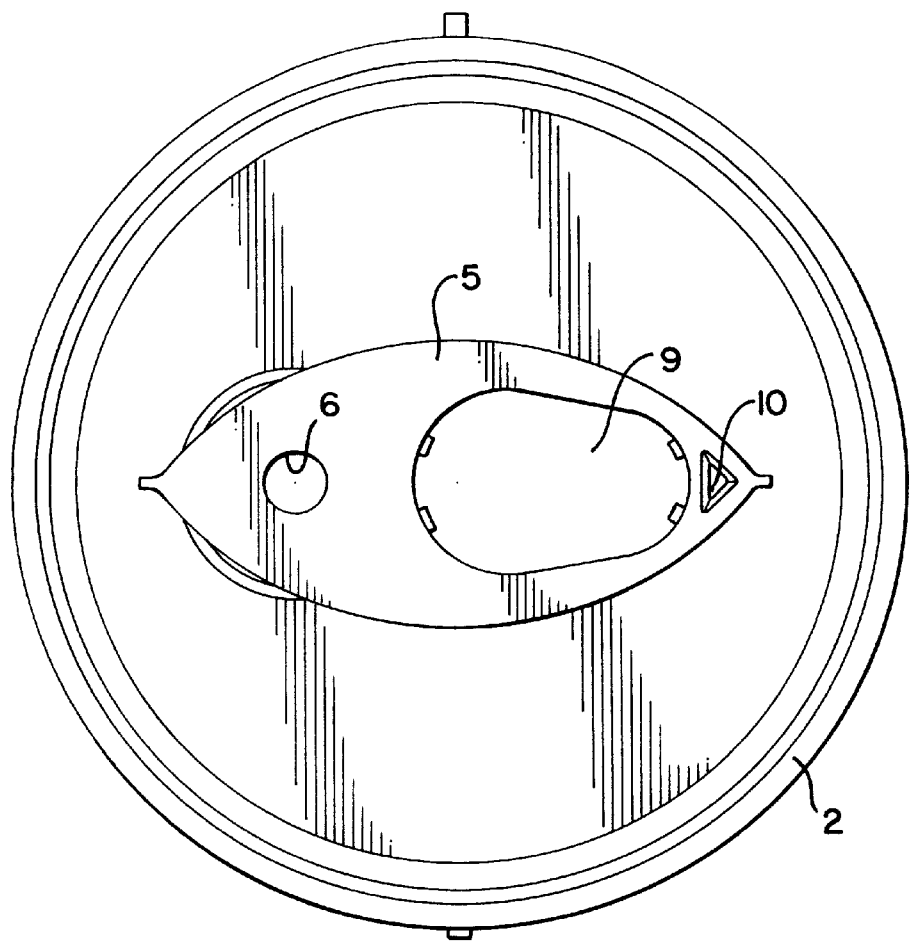
FIG. 2 is a planar view taken along line 2—2 of FIG. 1 providing an upward view of the lower surface of the collector cap with a disposable bag in place.
Figure 3:
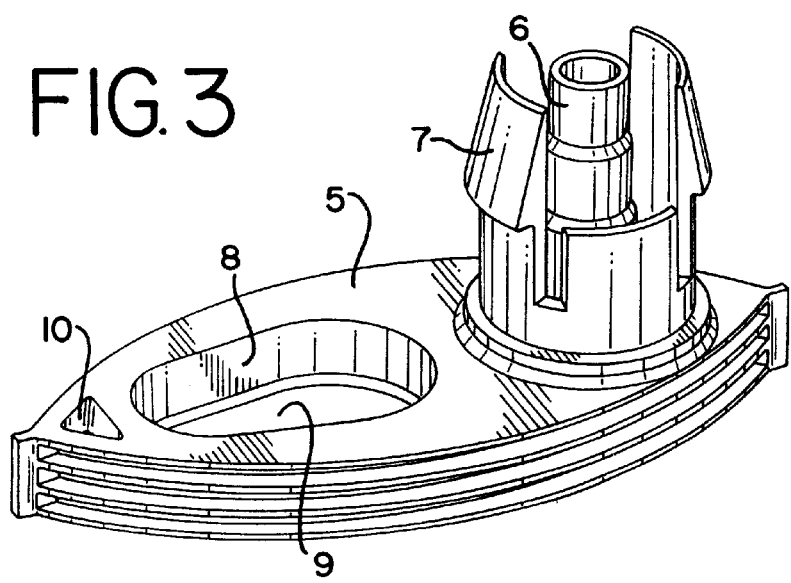
FIG. 3 is a perspective view of the rigid top component of a disposable bag shown in FIG. 1.

As shown in FIGS. 1–3, a rigid top component 5 of a flexible disposable bag B is attached to the underside of the vessel cap 2. The rigid top component 5 consists of a boat-shaped plate from which a connection nipple 6 passes upwardly through the vessel-cap aperture 4. The nipple 6 retains the push-on drainage tube leading to the patient indicated by arrow P with a snap-lock action fitting 7 having upwardly extending fingers concentrically arranged about the nipple 6 provided at the upper terminus of the nipple 6. There is provision for a seal between the top plate 5 of the bag B and the vessel cap 2 in order to make an airtight seal between the two parts. The snap-lock fitting 7 passes through the aperture in the cap 4 and then snaps into the retaining position as shown in FIG. 1. The rigid plate 5 of the disposable bag is thereby firmly attached to the lower surface of the cap 2 in the fully installed position. When the drainage tube and the connecting tube are fully and operatively connected to the source of suction, the interior of the vessel 1 is then fully sealed off from the exterior environment.

An additional aperture 8 containing a membrane 9 is provided on the top plate 5 of the bag. This membrane 9 is impermeable for liquid fluids but permeable for gases or air whereby it offers very slight resistance.

An additional aperture 10 which is normally closed by a knock-out element or frangible diaphragm (i.e., plug) 11 is provided in the top plate 5 of the bag B. When a bag B is being emptied, this aperture could be used for venting purposes, if required, to facilitate the draining off—through the nipple 6—of the fluid collected. As a rule, pressing the wall of the bag to urge fluid outflow is sufficient to empty the bag.

If the source of vacuum is now set in operation with a bag fitted underneath the cap 2 (with the top plate 5 of the bag B firmly attached or clamped to the cap and tubes connected to the vacuum source and to the patient), i.e. with a suction effect being created through the connector, air is first evacuated at the upper end of the vessel in the spaces designated A. The side walls of the bag B are then opened up and drawn in the direction of the walls of the vessel 1. The air inside the bag is then drawn off through the membrane 9, which has also served as an air restrictor on air outflow from the bag, creating a vacuum which ensures that the fluid to be drained of is drawn into the bag B via the tube connected to the patient, but maintaining a pressure differential between the interior of the vessel 1 and the bag interior.

The simple design of this invention, particularly the rigid top plate 5 of the disposable bag, provides a device which allows fluids to be drained off into a disposable bag with a minimum of design complexity. At the same time, this device is also suited to normal use, i.e. the draining off of fluids directly into the rigid vessel 1. For this purpose, either the same cap 2 can be used or a separate cap which has a connection for a drainage tube and a connection for a vacuum source may be used according to the invention.

Although particular embodiments of the invention have been discussed in detail for illustrative purposes, it will be recognized that variations and modifications of the disclosed device and method of use thereof lie within the scope of the appended claims and their legal equivalents.

What is claimed is:

1. A device for collecting fluid drainage in a collection vessel under vacuum operation, comprising:
    a sealable container having an interior capable of being evacuated;
    a collapsible collection bag receivable within the container interior and supported by an external support having at least one wall proximate to the collection bag;
    a sealing cap for sealing the collection bag with an airtight seal to a separate vessel cap, the sealing cap having a connection for a drainage tube for receiving fluid drainage and further including a snap-lock fitting member, and a port for communicating with a vacuum source, the vessel cap having a connection for a vacuum source and an opening for connection with the snap-lock fitting member, the vessel cap connection for a vacuum source being open to the container interior and further communicating with the collection bag port and creating a pressure differential between the container interior and the collection bag when vacuum is applied, wherein initial vacuum evacuation of the collection bag brings the collection bag into supporting contact by the external support and maintains the collection bag in an expanded condition for receiving a drainage collection under vacuum operation.

2. The collection device of claim 1, wherein the external support is a rigid external vessel for receiving substantially the entirety of the collection bag in supporting contact with the external support.

3. The collection device of claim 1, including a membrane in the collection bag sealing cap which is permeable to gaseous fluid outflow and comprises an airflow restriction under vacuum operation, but is substantially impermeable to liquid fluid outflow during extraction of extraneous gaseous fluids contained within the collection bag.

4. The collection device of claim 1, wherein the collection bag is disposable.

5. The collection device of claim 1, wherein the sealing cap of the collection bag is relatively rigid and supports a relatively flexible liquid fluid collection portion.

6. The collection device of claim 5, wherein the sealing cap is removably secured with an airtight seal to a rigid external support vessel for enhancing initial vacuum evacuation of the collection bag and support of a relatively flexible fluid collection portion by the external support vessel.

7. The collection device of claim 6, comprising a relatively rigid sealing cap for supporting the flexible fluid collection portion.

8. The collection device of claim 1, wherein the sealing cap includes an inlet for fluidic communication with the drainage tube.

9. The collection device of claim 8, wherein the sealing cap includes upwardly-extending fingers concentrically arranged with the inlet and defining an annulus for receiving and engaging the drainage tube with a snap-action engagement.

10. The collection device of claim 8, further comprising a plug provided in the sealing cap, whereby the plug is removed to enhance discharge of fluids contained in the collection bag.

11. A collection bag for use with a collection device for collecting fluid drainage in a collection vessel under vacuum operation, comprising:
    a relatively flexible fluid collection bag portion; and
    a two-piece closure for a substantially airtight engagement with a rim of the collection vessel within which the collection bag is received, said closure having a relatively inflexible sealing cap portion to which the collection bag portion is sealed for supporting the fluid collection bag portion, the sealing cap portion including a drainage tube inlet and a port for communicating with a vacuum source, and a vessel cap portion, the vessel cap portion being configured to be received in an airtight sealing arrangement with the collection vessel, the vessel cap portion having a connection for a vacuum source and an opening for connection with the sealing cap portion drainage tube inlet, and a snap-fit connecting element for joining the sealing cap portion and the vessel cap portion at the drainage tube inlet, the connection for the vacuum source being open to the interior of the collection vessel and further communicating with the collection bag portion, whereby a pressure differential is created between the collection vessel and the collection bag portion when vacuum is applied.

12. The collection bag of claim 11, further comprising a frangible diaphragm provided in the sealing cap portion, whereby the diaphragm is breached to enhance discharge of fluids contained in the collection bag portion.

13. The collection bag of claim 11, further comprising a membrane in the collection bag which is permeable to gaseous fluid outflow under vacuum operation, but is substantially impermeable to liquid fluid outflow during extraction of extraneous gaseous fluids contained within the collection portion.

14. The collection bag of claim 11, wherein the collection bag is disposable.

15. A fluid drainage and collection device, comprising:

a container, said container defining an interior space that can be subjected to a reduced pressure and an opening to said interior space;

a collapsible collection bag received within said container interior space, said collection bag having a rigid sealing cap closing said collection bag, said sealing cap having a first opening for fluid being collected and a second opening for connection to a source of vacuum;

a vessel cap for closing said container opening, said vessel cap including an inlet in communication with said first opening of said collection bag, and an outlet for connection with a source of vacuum as well as communicating with said second opening of said collection bag, and a snap-fit connector carried on one of said sealing cap and vessel cap joining said vessel cap and said sealing cap at said first opening and said inlet, wherein said collection bag and said cap are formed as separate parts and then joined as an integral unit which is attached to said container opening in sealing engagement therewith.

16. The device of claim 15 wherein said outlet further includes a conduit structure which is open to said container interior space as well as said collection bag second opening, and an element for restricting the outflow of air from said collection bag in the form of a membrane positioned within said second opening which is permeable to gas but relatively impermeable to liquid, whereby a single source of vacuum applied to said outlet of said cap provides a pressure differential between said container interior space and said collection bag causing said collection bag to expand within said interior space.

17. The device of claim 16 wherein the sealing cap includes upwardly-extending fingers concentrically arranged with said inlet and defining an annulus for receiving and engaging a drainage tube with a snap-action engagement.

* * * * *